(12) United States Patent
Moga et al.

(10) Patent No.: US 8,888,757 B2
(45) Date of Patent: Nov. 18, 2014

(54) ACTIVE MICRONEEDLE ARRAY

(75) Inventors: Benjamin J. Moga, Madison, WI (US); David J. Beebe, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1258 days.

(21) Appl. No.: 12/473,028

(22) Filed: May 27, 2009

(65) Prior Publication Data

US 2010/0305518 A1 Dec. 2, 2010

(51) Int. Cl.
| | | |
|---|---|---|
| *A61M 31/00* | (2006.01) | |
| *A61B 17/20* | (2006.01) | |
| *A61M 5/00* | (2006.01) | |
| *A61M 25/00* | (2006.01) | |
| *A61M 5/32* | (2006.01) | |
| *A61M 37/00* | (2006.01) | |

(52) U.S. Cl.
CPC ... *A61M 37/0015* (2013.01); *A61M 2037/0046* (2013.01)
USPC .............. 604/506; 604/22; 604/264; 604/272

(58) Field of Classification Search
CPC ............... A61M 37/0015; A61M 2037/003; A61M 2037/0046; A61M 2037/0061; A61M 2205/0216; A61M 2210/04
USPC .............. 604/272, 173, 171, 506, 46, 22, 47, 604/191, 264, 239; 606/186
See application file for complete search history.

(56) References Cited

U.S. PATENT DOCUMENTS

| | | | |
|---|---|---|---|
| 6,256,533 B1 * | 7/2001 | Yuzhakov et al. | 604/21 |
| 2004/0087992 A1 * | 5/2004 | Gartstein et al. | 606/186 |
| 2009/0093775 A1 * | 4/2009 | Raju et al. | 604/272 |
| 2009/0163872 A1 * | 6/2009 | Tekulve | 604/164.11 |

\* cited by examiner

*Primary Examiner* — Kevin C Sirmons
*Assistant Examiner* — Shefali Patel
(74) *Attorney, Agent, or Firm* — Boyle Fredrickson, S.C.

(57) ABSTRACT

An active microneedle array and method are provided for penetrating an outer layer of an epidermis. The active microneedle array includes a base having first and second sides. The first side of the base is engageable with the epidermis. A microneedle projects from the first side of the base. The microneedle is moveable between a first initial configuration and a second deformed configuration in response to engagement with the epidermis so as to form a passageway therein.

18 Claims, 4 Drawing Sheets

ACTIVE MICRONEEDLE ARRAY

FIELD OF THE INVENTION

This invention relates generally to microneedle arrays, and in particular, to an active microneedle array designed to penetrate the outer layer of the epidermis and subsequently create and maintain a sufficiently sized hole to allow fluid flow past the outer layer thereof.

BACKGROUND AND SUMMARY OF THE INVENTION

Transdermal delivery of drugs is achieved by a number of technologies including high velocity particles, hydration, chemical enhancement, iontophoresis, ultrasound, and microneedle arrays (μarrays). In general, microneedles are defined as needles having lengths in the range of 1-1000 micrometers (μm). Microneedles are designed to penetrate the outer layer of the epidermis in such a manner as to not compromise the underlying nerves and blood vessels of the dermal layer. In this manner, microneedles are an effective way of administering both small and large molecule drugs without causing pain or bleeding. When microneedles are assembled in a pattern, such as in an array, they are an effective way to breech a substantial surface area of the epidermis in a minimally invasive way.

In view of the foregoing, it can be appreciated that μarrays have the potential to be integrated in a delivery device that can be reliably used by a patient without the oversight of a healthcare professional. By way of example, transdermal delivery has the ability to elicit a favorable immune reaction in response to vaccines since the point of delivery is ripe with molecules involved in the immune response. It has been found that by delivering DNA directly into the intracellular compartment via a transdermal delivery process, approximately 1,000 times less DNA may be used than conventional needle and syringe delivery to achieve a comparable response. However, the transdermal delivery process is based on the high velocity approach to transdermal delivery. This approach requires a bulky device for purposes of administration and microscopic gold particles to be coated with the DNA plasmid to act as a carrier. Currently, all commercial μarray efforts use either a drug coated onto the surface of the μarray or are constructed of a biodegradable polymer infused with a drug. Both embodiments limit the maximum dose that may be delivered by the μarray. In addition, both of these prior μarrays require pharmaceuticals to be reformulated, thereby adding substantial development and regulatory costs to μarrays. As a result, the use of μarrays is not a delivery option for many drugs. Hence, a μarray that could administer a drug without the need of a coated carrier particle and has the advantage of being housed in a small, disposable device would be highly desirable.

Therefore, it is a primary object and feature of the present invention to provide an active microneedle array designed to penetrate the outer layer of the epidermis and subsequently create and maintain a sufficiently sized hole to allow fluid flow past the outer layer.

It is a further object and feature of the present invention to provide an active microneedle array designed to penetrate the outer layer of the epidermis that allows for the administration of a drug.

It is a still further object and feature of the present invention to provide an active microneedle array designed to penetrate the outer layer of the epidermis that may be housed in a small, disposable device.

It is a still further object and feature of the present invention to provide an active microneedle array designed to penetrate the outer layer of the epidermis that is simple to use and inexpensive to manufacture.

In accordance with the present invention, an active microneedle array is provided for penetrating the outer layer of the epidermis. The active microneedle array includes a base having first and second sides. The first side of the base is engageable with the epidermis. A microneedle projects from the first side of the base, The microneedle is moveable between a first initial configuration and a second deformed configuration in response to engagement with the epidermis so as to form an opening therein.

The microneedle is free of coatings and is defined by first and second flexible sidewalls. Each sidewall includes an inner surface partially defining a flowpath therebetween. In a first embodiment, the sidewalls are generally parallel to each other in a spaced relationship with the microneedle in the initial configuration. The sidewalls engage each other with the microneedle in the deformed configuration. The base includes an aperture extending between the first and second sides thereof. The aperture is positioned adjacent the microneedle.

In accordance with a further aspect of the present invention, an active microneedle array is provided for penetrating an outer layer of the epidermis. The active microneedle array includes a base having first and second sides. The first side is engageable with the epidermis. A microneedle projects from the first side of the base. The microneedle is moveable between a first initial configuration and a second deformed configuration. An aperture extends between the first and second sides of the base. The aperture is positioned adjacent the microneedle. The microneedle is urged to the deformed configuration in response to engagement with the epidermis so as to form a passageway in the outer layer of the epidermis.

The microneedle is free of coatings and, in a first embodiment, the microneedle is defined by first and second flexible sidewalls. Each sidewall includes an inner surface partially defining a flowpath therebetween. The sidewalls are generally parallel to each other in a spaced relationship with the microneedle in the initial configuration. The sidewalls engage each other with the microneedle in the deformed configuration. The aperture may be positioned between the first and second sidewalls. Alternatively, the microneedle may extend along an axis in the initial configuration. The microneedle may twist about the axis to move to the deformed configuration.

In accordance with a still further aspect of the present invention, a method of penetrating an outer layer of an epidermis is provided. The method includes the steps of providing a microneedle array having a base and microneedle projecting therefrom. The microneedle has an initial configuration. The epidermis is penetrated with the microneedle such that the microneedle deforms to a deformed configuration and creates a passageway in the outer layer of the epidermis.

The step of penetrating the epidermis with the microneedle may include the additional step of twisting the microneedle from the initial configuration to the deformed configuration. Alternatively, the microneedle may be defined by first and second flexible sidewalls. The sidewalls are generally parallel to each other in a spaced relationship with the microneedle in the initial configuration. With the microneedle in the deformed configuration, the sidewalls engage each other. It is contemplated to provide an aperture through the base. The aperture through the base may be position at a location between the first and second sidewalls or at a location adjacent the microneedle.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings.

DETAILED DESCRIPTION OF THE DRAWINGS

Figure 1:
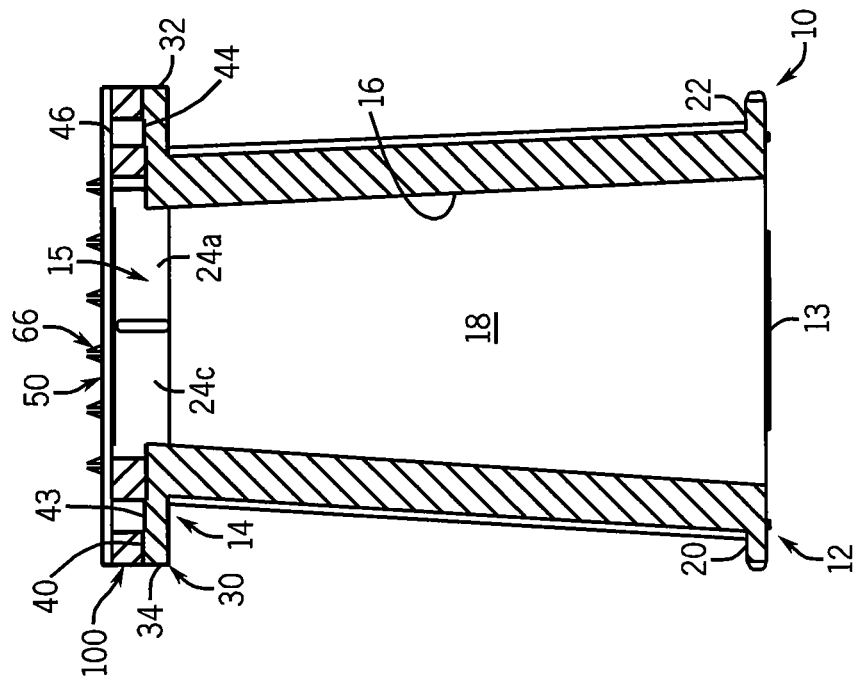
FIG. 1 is an isometric view of a connector incorporating a microneedle array in accordance with the present invention.
Figure 2:
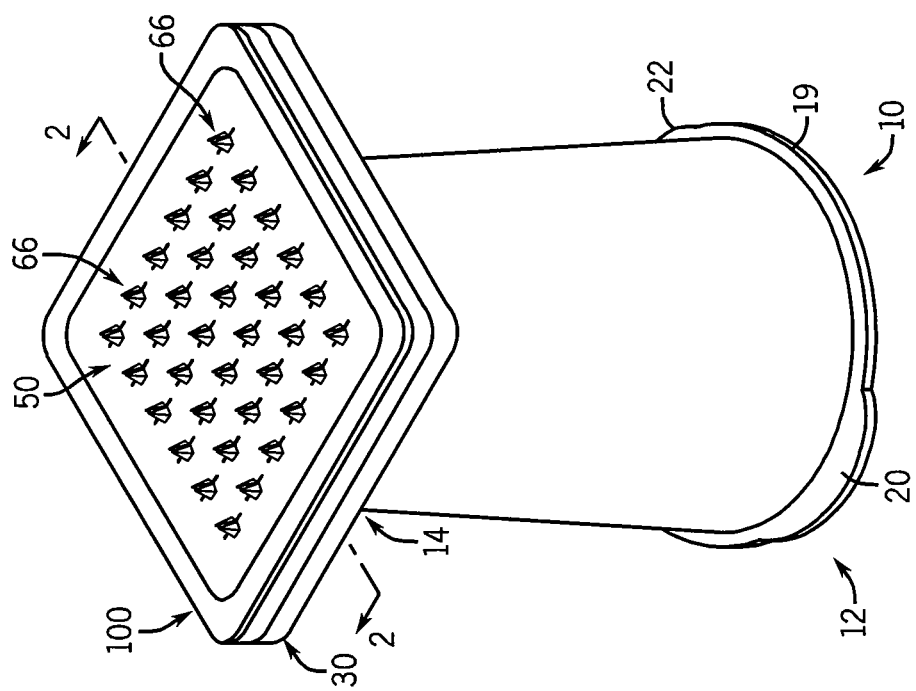
FIG. 2 is a cross-sectional view of the connector taken along line 2-2 of FIG. 1.
Figure 3:
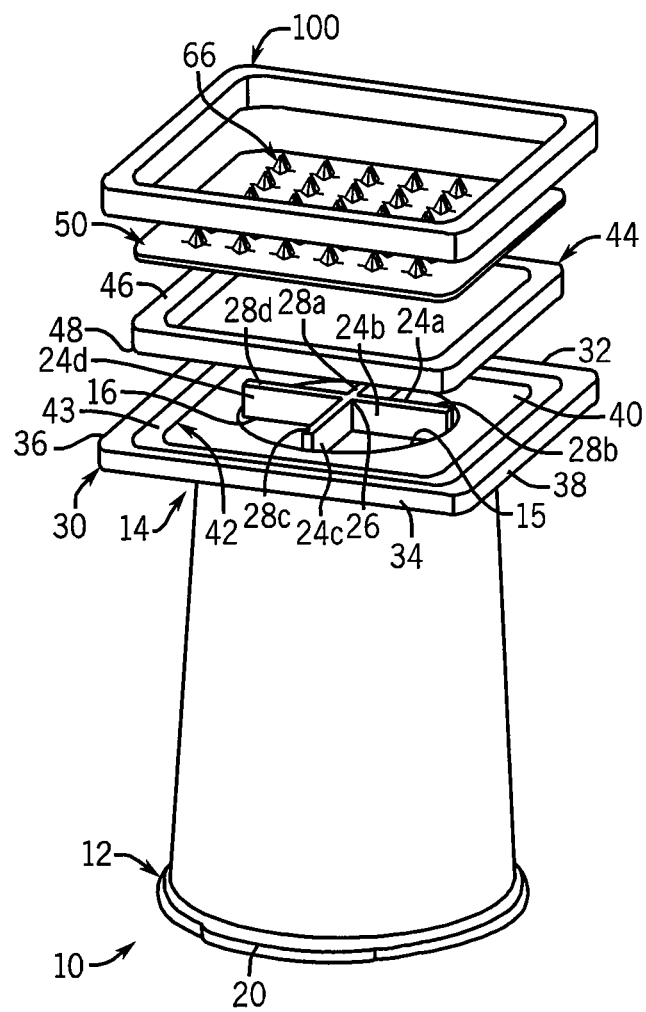
FIG. 3 is an exploded, isometric view of the connector of FIG. 1.

Referring to FIG. 1-3, a connector incorporating a microneedle array in accordance with the present invention is generally designated by the reference numeral 10. As hereinafter described, connector 10 is connectable to a conventional luer-loc syringe in a conventional manner. More specifically, connector 10 is generally tubular and includes first and second opposite ends 12 and 14, respectively. First and second ends 12 and 14, respectively, define corresponding first and second openings 13 and 15, respectively. Inner surface 16 of connector 10 defines passageway 18 therethrough to accommodate the flow of fluid between first and second openings 13 and 15, respectively, in connector 10. Flange 19 extends about first end 12 of connector 10 and includes circumferentially spaced mounting tabs 20 and 22 project outwardly therefrom. Mounting tabs 20 and 22 are adapted for engaging corresponding threads in a sleeve on the luer-loc syringe in order to form a leak-free connection therebetween.

A plurality of support spokes 24a-24d are positioned within passageway 18 adjacent second end 14 of connector 10. Support spokes 24a-24d project radially outward from central hub 26 and terminate at inner surface 16 of connector 10. Outer surfaces 28a-28d of support spokes 24a-24d project from second end 14 of connector 10. In addition, support platform 30 projects radially outward from second end 14 of connector 10. Support platform 30 has a generally rectangular configuration and is defined by first and second sides 32 and 34, respectively, and first and second ends 36 and 38, respectively. Support platform 30 further includes mounting surface 40 having a recessed surface 43 formed therein that defines a generally rectangular-shaped groove 42. Groove 42 extends about opening 15 in second end 14 of connector 10 and is adapted for receiving a corresponding gasket 44 therein.

As best seen in FIG. 3, gasket 44 has a generally rectangular configuration corresponding in size and shape to groove 42 in mounting surface 40 of support platform 30. Gasket 44 includes upper and lower surfaces 46 and 48, respectively. Lower surface 48 of gasket 44 is seated on and forms a mating, leak-free relationship with recessed surface 43 in mounting surface 40 of support platform 30. Upper surface 46 of gasket 44 is adapted for receiving microneedle array 50 thereon, as hereinafter described.

Figure 4:
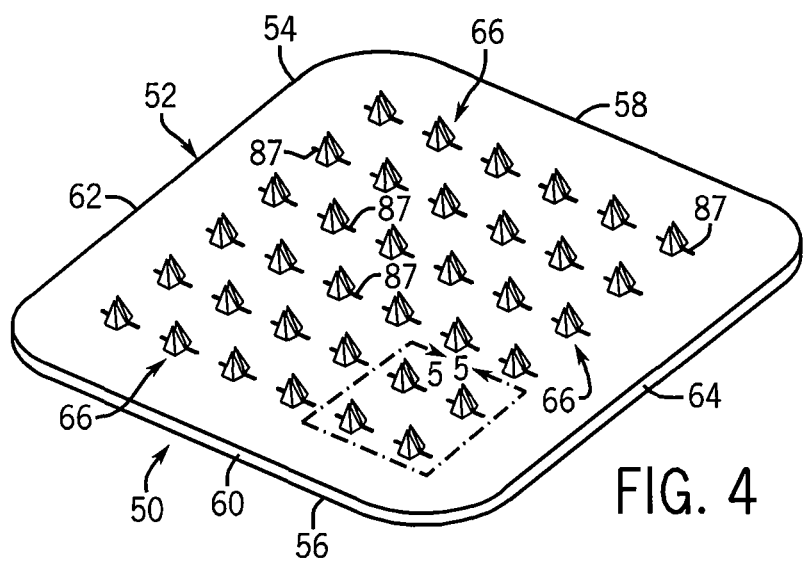
FIG. 4 is a first embodiment of an isometric view of a microneedle array in accordance with the present invention.
Figure 5:
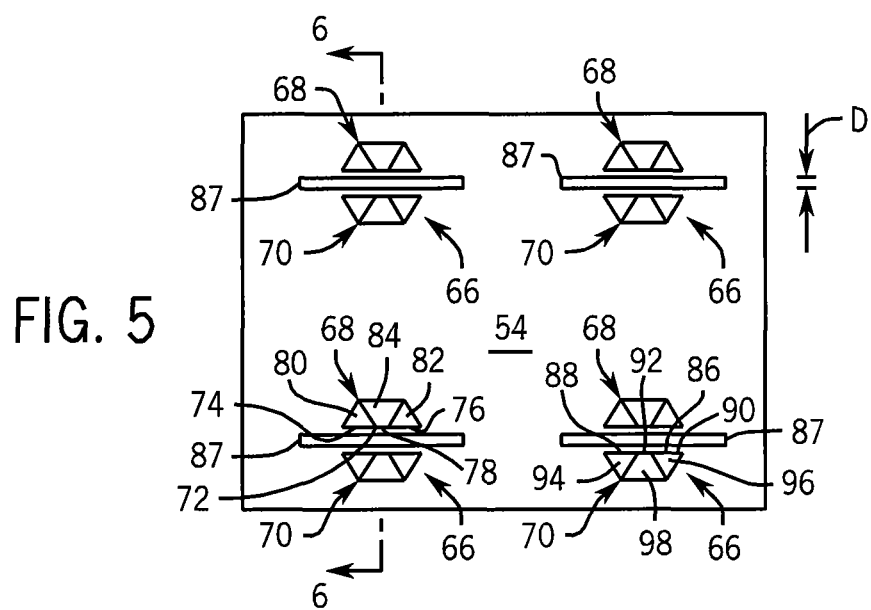
FIG. 5 is an enlarged view of the microneedle array of the present invention taken along line 5-5 of FIG. 4.

Referring to FIG. 4, microneedle array 50 includes sheet 52 having a generally rectangular configuration corresponding in size and shape to gasket 44 and being defined by outer and inner surfaces 54 and 56, respectively. The outer periphery of sheet 52 is defined by first and second sides 58 and 60, respectively, and first and second ends 62 and 64, respectively. In the depicted embodiment, the corners of sheet 52 are rounded. However, the corners of sheet 52 may have other configurations without deviating from the scope of the present invention.

Microneedle array 50 further includes a plurality of microneedle pairs, generally designated by the reference numeral 66, projecting from outer surface 54 of sheet 52. The plurality of microneedle pairs 66 are arranged in a series of rows and columns. Each microneedle pair of the plurality of microneedle pairs 66 is identical in structure. As such the following description of a microneedle pair is understood to describe all of the plurality of microneedle pairs 66 as if fully described herein.

Microneedle pair 66 includes first and second needles 68 and 70, respectively, fabricated from an elastic material, for reasons hereinafter described. First and second needles 68 and 70, respectively, have a height preferentially in the range of 200 μm to 900 μm, and more preferentially, in the range of 300 μm-750 μm. It is contemplated for first and second needles 68 and 70, respectively, to be free of drugs coated onto the outer surfaces thereof. However, drugs may be coated onto the outer surfaces thereof if desired.

First needle 68 is defined by inner wall 72 projecting from outer surface 54 of sheet 52 at an angle generally perpendicular. Inner wall 72 includes first and second sides 74 and 76, respectively, and terminates at apex 78. First and second sidewalls 80 and 82, respectively, extend from corresponding sides 74 and 76, respectively, of inner wall 72 at a predetermined angle thereto. First and second sidewalls 80 and 82, respectively, project from outer surface 54 of sheet 52 at an acute angle thereto and terminate at apex 78. Outer wall 84 extends between first and second sidewalls 80 and 82, respectively, and project from outer surface 54 of sheet 52 at an acute angle thereto. Outer wall 84 terminates at apex 78.

Second needle 70 is defined by inner wall 86 projecting from outer surface 54 of sheet 52 at an angle generally perpendicular. Inner wall 86 of second needle 70 is generally parallel to and spaced from inner wall 72 of first needle 68 by distance D so as to define a fluid flowpath therebetween. Aperture 87 extends through sheet 52 at a location between inner wall 86 of second needle 70 and inner wall 72 of first needle 68. Inner wall 86 of second needle 70 includes first and second sides 88 and 90, respectively, and terminates at apex 92. First and second sidewalls 94 and 96, respectively, extend from corresponding sides 88 and 90, respectively, of inner wall 86 of second needle 70 at predetermined angles thereto. First and second sidewalls 94 and 96, respectively, of second needle 70 project from outer surface 54 of sheet 52 at an acute angle thereto and terminate at apex 92. Outer wall 98 of second needle 70 extends between first and second sidewalls 94 and 96, respectively, and projects from outer surface 54 of sheet 52 at an acute angle thereto. Outer wall 98 of second needle 70 terminates at apex 92.

Referring back to FIG. 3, in order to mount microneedle array 50 on connector 10, a first portion of inner surface 56 of microneedle array 50 adjacent the outer periphery thereof is positioned on upper surface 46 of gasket 44. A central portion of inner surface 56 of microneedle array 50 is positioned on outer surfaces 28a-28d of support spokes 24a-24d. Connection member 100 is positioned over the outer periphery of sheet 52 and is operatively connected to support platform 30 to secure sheet 52 in position.

Figure 6:
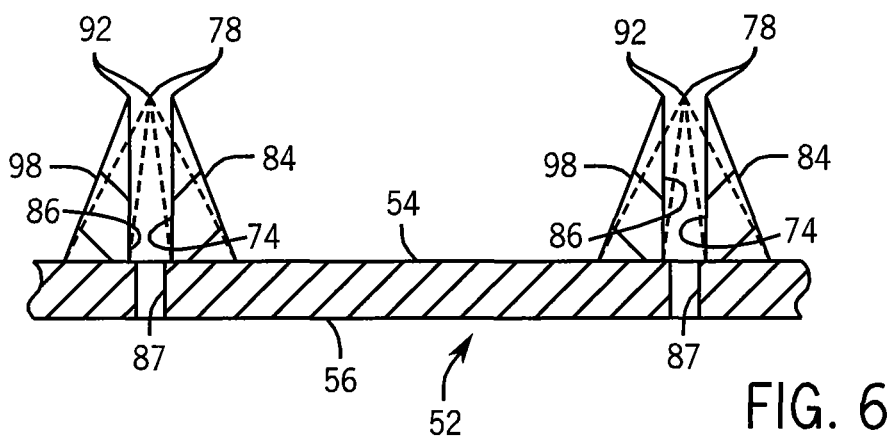
FIG. 6 is a cross-sectional view of the microneedle array of the present invention taken along line 6-6 of FIG. 5.

In operation, it is intended for each microneedle pair 66 to preferentially collapse, flex, twist, or bend in a predetermined manner so as to preferentially collapse into each other upon insertion into the outermost layer of the epidermis or skin of an individual. More specifically, as the apexs 78 and 92 of first and second needles 68 and 70, respectively, of each microneedle pair 66 engage the skin of an individual, first and second needles 68 and 70, respectively, are urged toward each other, shown in phantom in FIG. 6. After piercing the skin of the individual and forming a perforation therethrough, first and second needles 68 and 70, respectively, are urged by their elastic properties toward their original position. The restoring force generated by the elastic material of the first and second needles 68 and 70, respectively, provides a constant force on first and second needles 68 and 70, respectively, and acts to keep the perforation in the skin open. That is, the constant force on first and second needles 68 and 70, respectively, acts against the skin's (tissue) natural tendency to close the perforation. Once the perforations are formed in the skin by the plurality of microneedle pairs 66, a user engages the syringe so as to cause fluid to be delivered through passageway 18 in connector 10. The fluid continues to flow under pressure of the syringe between first and second needles 68 and 70, respectively, and through the apertures 87 in sheet 52. It can be appreciated that the perforations formed in the skin of an individual by the plurality of microneedle pairs 66 allow for the fluid to flow past the microneedle pairs 66 and across the skin barrier.

Figure 7:
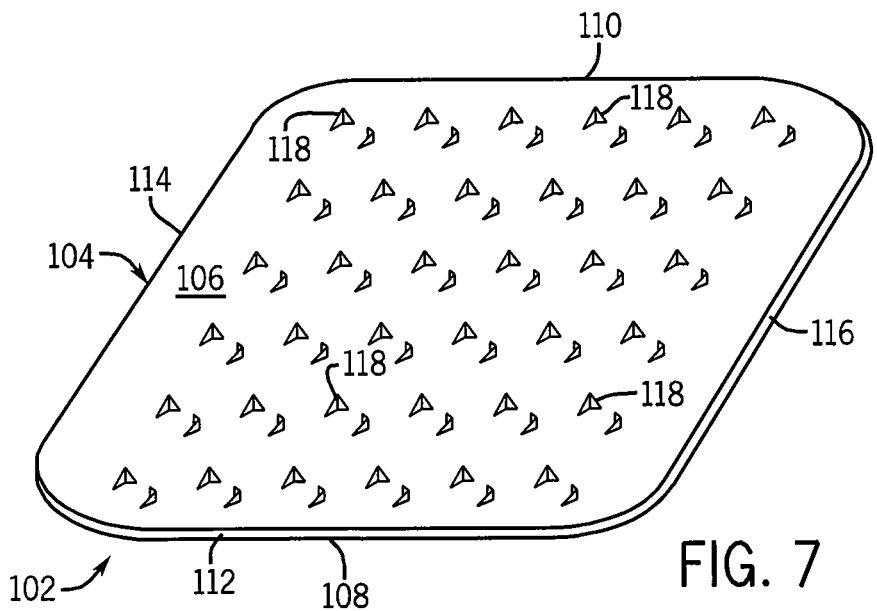
FIG. 7 is a second embodiment of an isometric view of a microneedle array in accordance with the present invention.
Figure 8:
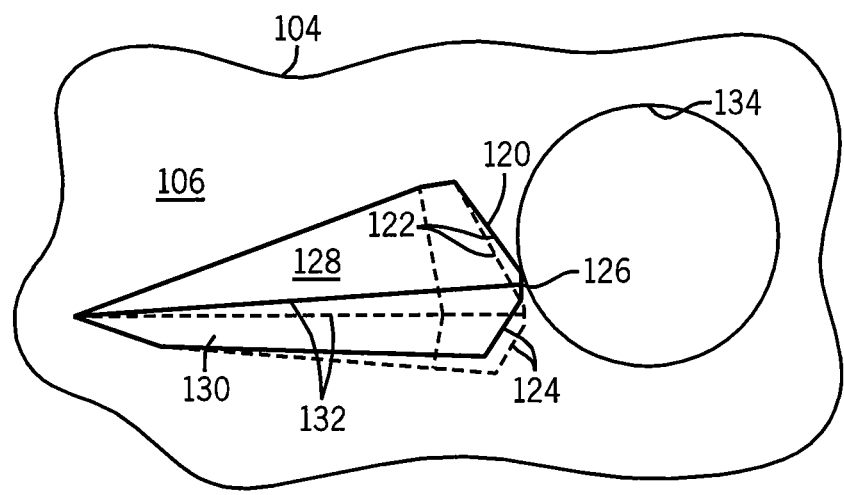
FIG. 8 is an enlarged, top plan view of a portion of the microneedle array of FIG. 5.

Referring to FIGS. 7-8, an alternate embodiment of a microneedle array in accordance with the present invention is generally designated by the reference numeral 102. Microneedle array 102 includes sheet 104 having a generally rectangular configuration corresponding in size and shape to gasket 44 and being defined by outer and inner surfaces 106 and 108, respectively. The outer periphery of sheet 104 is defined by first and second sides 110 and 112, respectively, and first and second ends 114 and 116, respectively. In the depicted embodiment, the corners of sheet 104 are rounded. However, the corners of sheet 104 may have other configurations without deviating from the scope of the present invention.

Microneedle array 102 further includes a plurality of microneedles, generally designated by the reference numeral 118, projecting from outer surface 106 of sheet 104. Microneedles 118 are fabricated from an elastic material and arranged in a series of rows and columns. Each microneedle 118 is identical in structure, and as such, the following description of microneedle 118 is understood to describe all of the microneedles 118 of microneedle array 102 as if fully described herein. It is contemplated for microneedles 118 to have a height preferentially in the range of 200 µm to 900 µm, and more preferentially, in the range of 300 µm-750 µm. It is further contemplated for microneedles 118 to be free of drugs coated onto the outer surfaces thereof. However, drugs may be coated onto the outer surfaces thereof if desired.

Referring to FIG. 8, mirconeedle 118 is defined by inner wall 120 projecting from outer surface 106 of sheet 104 at an angle thereto. Inner wall 120 includes first and second sides 122 and 124, respectively, and terminates at apex 126. First and second sidewalls 128 and 130, respectively, extend from corresponding sides 122 and 124, respectively, of inner wall 120 and converge at upper edge 132. First and second sidewalls 128 and 130, respectively, project from outer surface 106 of sheet 104 at an acute angle thereto and terminate at apex 126. Aperture 134 extends through sheet 104 at a location adjacent inner wall 120 of microneedle 118.

In operation, microneedle array 102 is substituted for microfluidic array 50 in connector 10. As herein after described, it is intended for microneedles 118 to preferentially collapse, flex, twist, or bend in a predetermined manner upon insertion into the outermost layer of the epidermis or skin of an individual. More specifically, as the apexs 126 of microneedles 118 engage the skin of an individual, first and second sidewalls 128 and 130 of microneedles 118 collapse, flex, twist, or bend in a predetermined manner, shown in phantom in FIG. 8. After piercing the skin of the individual and forming a perforation therethrough, first and second sidewalls 128 and 130, respectively, of microneedles 118 are urged by their elastic properties toward their original position. The restoring force generated by the elastic material of the microneedles 118 provides a constant force on first and second sidewalls 128 and 130, respectively, of microneedles 118 and acts to keep the perforation in the skin open. That is, the constant force on first and second sidewalls 128 and 130, respectively, of microneedles 118 acts against the skin's (tissue) natural tendency to close the perforation. Once the perforations are formed in the skin by microneedles 118, a user engages the syringe so as to cause fluid to be delivered through passageway 18 in connector 10. The fluid continues to flow under pressure of the syringe through the apertures 134 in sheet 104. It can be appreciated that the perforations formed in the skin of an individual by microneedles 118 allow for the fluid to flow across the skin barrier.

It can be appreciated that operation of microneedle pairs 66 and microneedles 118 of microneedle arrays 50 and 102, respectively, are dependent on the penetration force, velocity, and in general, control of the dynamic exploitation of stored potential energy. The penetration event may be further controlled by altering microneedle position, microneedle geometry, aperture size, and aperture location to effect the microneedle material reaction in response to release of the potential energy and resulting contact with the epidermis.

Various modes of carrying out the invention are contemplated as being within the scope of the following claims particularly pointing out and distinctly claiming the subject matter, which is regarded as the invention.

We claim:

1. An active microneedle array for penetrating an outer layer of an epidermis, comprising:
    a base having first and second sides, the first side engageable with the epidermis; and
    a microneedle projecting from the first side of the base and including first and second flexible sidewalls terminating corresponding apexes, the apexes of the first and second sidewalls of the microneedle moveable along an axis generally parallel to the base between a first initial configuration wherein the first and second sidewalls define a flowpath therebetween and a second deformed configuration wherein the first and second sidewalls are adjacent in response to engagement with the epidermis so as to facilitate the penetration of the outer layer by the microneedle,
    wherein:
        the microneedle has an elasticity, the elasticity urging the apexes of the first and second sidewalls of the microneedle towards the initial configuration after the penetration of the outer layer so as to form an opening in the outer layer.

2. The active microneedle array of claim 1 wherein the microneedle is free of a coating including a drug.

3. The active microneedle array of claim 1 wherein the first and second flexible sidewalls include inner surfaces partially defining the flowpath therebetween.

4. The active microneedle array of claim 3 wherein the sidewalls are generally parallel to each other in a spaced relationship with the microneedle in the initial configuration.

5. The active microneedle array of claim 1 wherein the base includes an aperture extending between the first and second sides thereof, the aperture being positioned adjacent the microneedle.

6. An active microneedle array for penetrating an outer layer of an epidermis, comprising:
 a base having first and second sides, the first side engageable with the epidermis;
 a microneedle projecting from the first side of the base, the microneedle including first and second sidewalls having a corresponding apexes moveable along an axis generally parallel to the base between a first initial configuration wherein the first and second sidewalls define a flowpath therebetween and a second deformed configuration wherein the first and second sidewalls are adjacent; and
 an aperture extending between the first and second sides of the base, the aperture being positioned adjacent the microneedle;
 wherein:
  the apexes of the first and second sidewalls are urged toward the initial configuration;
  the apexes of the first and second sidewalls move to the deformed configuration in response to engagement with the epidermis so as to facilitate the penetration of the outer layer by the microneedle; and
  the apexes of the first and second sidewalls are urged towards the initial configuration after the penetration of the outer layer by the microneedle so as to form a passageway therein.

7. The active microneedle array of claim 6 wherein the microneedle is free of a coating including a drug.

8. The active microneedle array of claim 6 wherein the first and second sidewalls of the microneedle include inner surfaces partially defining the flowpath therebetween.

9. The active microneedle array of claim 8 wherein the sidewalls are generally parallel to each other in a spaced relationship with the apexes in the initial configuration.

10. The active microneedle array of claim 8 wherein the aperture is positioned between the first and second sidewalls.

11. A method of penetrating an outer layer of an epidermis, comprising the steps of:
 providing a microneedle array having a base and a microneedle projecting therefrom, the microneedle terminating at first and second spaced apexes having an initial configuration;
 engaging the epidermis with the apexes of the microneedle such that the apexes of the microneedle move along an axis generally parallel to the base and deform from the initial configuration to a second deformed configuration and penetrate the outer layer of the epidermis to form a perforation therein; and
 generating a force on the epidermis with the microneedle in the perforation such that the microneedle acts to keep the perforation in the epidermis open to create a passageway in the outer layer.

12. The method of claim 11 wherein the step of engaging the epidermis with the apexes of the microneedle such that the apexes of the microneedle penetrate the outer layer of the epidermis includes an additional step of twisting the microneedle.

13. The method of claim 11 wherein the microneedle is defined by first and second flexible sidewalls.

14. The method of claim 13 wherein the sidewalls are generally parallel to each other in a spaced relationship with the apexes of the microneedle in the initial configuration.

15. The method of claim 13 wherein the sidewalls engage each other with the apexes of the microneedle in the deformed configuration.

16. The method of claim 13 further comprising a step of providing an aperture through the base.

17. The method of claim 16 wherein the aperture through the base is provided at a location between the first and second sidewalls.

18. The method of claim 11 further comprising a step of providing an aperture through the base at a location adjacent the microneedle.

* * * * *